(12) United States Patent
Saffarian

(10) Patent No.: US 8,721,543 B2
(45) Date of Patent: May 13, 2014

(54) DATA ANALYTICS SYSTEM

(76) Inventor: Arsham Andy Saffarian, Mahwah, NJ (US)

( * ) Notice: Subject to any disclaimer, the term of this patent is extended or adjusted under 35 U.S.C. 154(b) by 201 days.

(21) Appl. No.: 13/348,805

(22) Filed: Jan. 12, 2012

(65) Prior Publication Data

US 2012/0179012 A1 Jul. 12, 2012

Related U.S. Application Data

(60) Provisional application No. 61/461,007, filed on Jan. 12, 2011.

(51) Int. Cl.
*A61B 5/00* (2006.01)
*G06F 19/00* (2011.01)

(52) U.S. Cl.
CPC ..................... *G06F 19/34* (2013.01)
USPC .......................................................... 600/301

(58) Field of Classification Search
USPC .................................................. 600/300–301
See application file for complete search history.

(56) References Cited

U.S. PATENT DOCUMENTS

| | | | | |
|---|---|---|---|---|
| 5,954,640 A * | 9/1999 | Szabo | ........................... | 600/300 |
| 7,463,142 B2 * | 12/2008 | Lindsay | ................... | 340/539.12 |
| 7,953,613 B2 * | 5/2011 | Gizewski | ........................ | 705/3 |
| 8,002,701 B2 * | 8/2011 | John et al. | ..................... | 600/300 |
| 2003/0092972 A1 * | 5/2003 | Mantilla et al. | ............... | 600/300 |
| 2004/0034284 A1 * | 2/2004 | Aversano et al. | ............. | 600/300 |
| 2006/0293570 A1 * | 12/2006 | Croghan et al. | ............. | 600/300 |
| 2007/0033072 A1 * | 2/2007 | Bildirici | ........................... | 705/3 |
| 2007/0106127 A1 * | 5/2007 | Alman | ........................ | 600/300 |
| 2007/0129610 A1 * | 6/2007 | Squilla | ......................... | 600/300 |
| 2007/0173705 A1 * | 7/2007 | Teller et al. | .................. | 600/300 |
| 2007/0213600 A1 * | 9/2007 | John et al. | .................... | 600/300 |
| 2008/0033255 A1 * | 2/2008 | Essenpreis et al. | ........... | 600/300 |
| 2009/0124867 A1 * | 5/2009 | Hirsh et al. | ................... | 600/301 |
| 2010/0115548 A1 * | 5/2010 | Leyvi | .............................. | 725/34 |
| 2010/0191071 A1 * | 7/2010 | Anderson et al. | ............. | 600/301 |
| 2011/0105979 A1 * | 5/2011 | Schlaeper et al. | ........... | 604/5.01 |

* cited by examiner

*Primary Examiner* — Bill Thomson
*Assistant Examiner* — Bobby Soriano

(57) ABSTRACT

The invention includes a system and processes to gather and analyze data to monitor, track, and provide care. The major subsystems of the invention include the Medical Digital Assistant ("MDA"), Server, Monitoring Devices, Dispensing Devices, Server, Dashboard, and Application Software. The invention includes the method for conducting data acquisition, monitoring, analysis, and reporting to diagnose and treat medical conditions such as diagnosing and treating specific medical conditions such as fertility and congestive heart failure.

16 Claims, 4 Drawing Sheets

DATA ANALYTICS SYSTEM

This application claims the benefit of U.S. Provisional Application No. 61/461,007 filed Jan. 12, 2011.

FIELD OF THE INVENTION

This invention relates generally to the field of data gathering and analysis, and particularly methods, apparatuses, and systems for gathering and analyzing data to monitor, track, and provide care.

BACKGROUND OF THE INVENTION

Monitoring, tracking, and caring for patients—such as patients requiring monitoring under a court order, or patient with disabilities, chronic medical conditions, or pre and post surgery—requires continuous attention to resources which are often unavailable or unaffordable. Such problems may be exacerbated when patient are remotely located, or have chronic conditions that require long term continuous monitoring. The problem may also arise when conducting clinical trials where the care providers must monitor patient frequently, continuously and in real-time. The current solutions are limited because they only monitor one data at a time and do not have the capability of correlating the combination of the data.

Examples of problems addressed by this invention include:

Current methods of providing medical attention to chronically ill patients, or patient that have cognitive deficiencies due to age and/or other disabilities or during pre and post surgery requires the patient to remain in close proximity to medical staff, equipment, and hospital or medical facilities. This means that a patient must stay in a hospital or care home, resulting in excessive costs as well as the loss of independence.

Many epilepsy patient are unable to live untethered lives; preventing them from activities such as driving, bicycling, hiking, walking alone, living alone, holding jobs, and generally experiencing a normal independent life.

Medical staffs often have too many patients to keep track of changing conditions that may result in a patient requiring urgent attention or a change in care or medication.

The process of manually documenting/recording patient data often results in entry errors, loss of data, security violations, or a loss of the correlation between the patient data and the correct patient. These types of errors result in inefficiencies, or worse, incorrect procedures or prescriptions.

Universal worldwide immediate accessibility of current patient data continues to be a problem. The current trend of a patient being assigned to a pool of medical staff, versus being assigned a single caregiver, complicates the ability of having access to readily available current medical records. This is further complicated by the fact that the pool of medical personnel may reside in disparate distant geographic locations.

Remote rural patients have to travel long distances to access medical care for routine visits/tests, or to be monitored for extended periods of time. This problem also persists in urban areas where crowded cities with extensive traffic and sparse parking make it equally difficult to obtain medical care.

Individuals under court order, requiring monitoring for illegal substances or under house arrest, are currently able to easily disable or circumvent the monitoring equipment, preventing authorities from enforcing the intended court intentions.

Not knowing the location or physical/medical status of a child or loved one can cause stress and anxiety. Individuals in need of police or emergency medical assistance will often not receive prompt help, or may never receive needed help.

Patient/client data that is being remotely recorded (away from the security of a physical facility) can be lost or stolen, resulting in release of confidential patient/client information.

Not having information on the patient's status, both qualitative and quantitative (simultaneously captured/recorded, sometimes for an extended continuous period), prevents an informed decision from being made that would otherwise result in an early diagnosis or proactive action. For example, having simultaneous access to a patient's blood oxygen, weight, heart rate, activity level, etc., could be used for early prevention/detection of a heart attack.

Detecting the basal temperature of both humans and other animals continues to be problematic. Being able to continuously monitor and record temperature (while awake or asleep) can be used to detect ovulation, as well as provide an indicator for certain disorders such as thyroid.

Home/remote care of patients often requires knowledge of how to setup/program/configure/operate complex medical equipment, often beyond the capabilities of the patient. For example, administering the dosage of infusion pumps used to dispense insulin, providing chemotherapies, nitro derivatives, anti-thrombotics, etc.

Managing patients in home or remote settings is currently impractical in cases where the medical condition may not require any intervention for extended periods, but can change quickly requiring an immediate response or a medical emergency requiring the immediate attention/intervention of medical personnel. This requires the ability to monitor one or more events, make decisions based on those events that may include monitoring a different set of events and/or taking some other action such as dispensing medication or activating an alert.

The reaction of a patient to medications is never completely known, and this is especially true of patients taking multiple medications where the interaction of multiple medications is frequently not tested or not known.

Patients are often asked to complete lengthy questionnaires that include irrelevant data. This is an inefficient and annoying practice that results in an overwhelming amount of irrelevant data that is either ignored by medical personnel or results in crucial data being buried and missed amongst all the irrelevant data.

Properly diagnosing and managing remote patients often requires being able to see the patient or the patient's medical equipment to monitor vital signs and other physiological and biological data.

The price per bit of transferring data via wireless data networks is expensive. This limits the amount of data that can affordably be transferred for many applications.

Physicians are not always aware of the patient's activities and symptoms outside the clinic. For example, when a patient complains about chest pain, the patient may not remember or been aware of other indicators which may help diagnose the problem such as activities, blood pressure, body temperature, etc.

Another problem for drug clinical trials is the preference to monitor patients more closely outside the clinics in their normal life while taking the drug and/or following certain treatments, both of which are outside the control and access of medical personnel.

This invention provides a solution to all these problems with a system and process capable of capturing and monitoring a patient's biological and physiological data, the capability to interactively communicate remotely, and enable actions to provide patient care.

BRIEF SUMMARY OF THE INVENTION

From a medical perspective, a patient's discomfort comes from the seemingly impersonal world of medical care, rather than the disease itself, including therapy side effects, lack of timely communication, professionals' misjudgments, improper treatments, medical errors, and endless paperwork. This invention is a interactive wireless patient monitoring platform that provides an integrated and secure solution for managing outpatient care and diagnostic information. It has no physical boundaries, allowing Healthcare professionals to stay connected with their patients anywhere, anytime. This unique holistic approach to next-generation health management is a flexible and scalable platform, delivering innovations that healthcare professionals can use to collect patient therapy information, perform research and analyze data—all in real-time.

This invention has been driven by two major trends:

Technology trends: Network technologies such as 3G, WiMAX and LTE have emerged as candidate radio technologies to support the Mobile Internet with ubiquitous connectivity. In addition, all IP architectures are becoming critical elements in the economical delivery of ubiquitous mobile broadband services. As these technologies migrate toward the 4G vision, mobile broadband services will be delivered with increased performance capabilities and improved economics. Mobile broadband technology delivers throughput speeds of 2 MB to 10 MB/second, and as the Mobile Internet proliferates, a completely new generation of service and end-user applications will emerge. To achieve profitability and differentiation in this complex world of the emerging Mobile Internet, operators, enterprises, software developers and applications and content providers all face a new Mobile Internet ecosystem.

Healthcare high cost: The United States last year spent an estimated $2.5 trillion—18 percent of its GDP on health care. Much of that spending was for costly hospital care, often delivered long after the onset of chronic problems that could have been better managed early on. This invention improves Patients' quality of care while increasing operational efficiencies within Healthcare organizations.

This invention provides a solution to all these problems with a system and process capable of capturing and monitoring patients and individuals biological and physiological data and the capability to interactively communicate remotely. Such data includes, but is not limited to an individual's vitals, blood sugar, blood count, medication concentration, presence of drugs/alcohol, heart/brain electrical activity, velocity, acceleration, physical location, being able to see the patient's appearance or the patient's medical equipment, such as video.

The invention may use available encryption techniques to record patient/client data, processes to aggregate and compress data to minimize data transmission charges, and may purge patient/client data from the recording device after successfully transmitting, wired or wirelessly, the patient/client data to a secure Server.

The invention may take action based on the recorded data, or received requests, transmitted wired or wirelessly. Actions taken by the system may include, but not limited to: altering the dispensing of medication, altering medical equipment such as pacemakers, defibrillators, or other equipment; sending alerts (wired or wirelessly) to specific individuals, a secure Server, Police, emergency medical personnel; enabling or disabling (wired or wirelessly) devices such as automobiles, audio/visual alarms, et cetera.

The invention may include an intelligent questionnaire process that is able to change questions asked based on responses of previous questions.

The invention may include a data fusion function where patient responses are included and aggregated along with other data and processed via a decision matrix, tree, or process to help provide potential diagnosis. Data may include patient subjective data such as vital signs, diary, behaviors, adverse reactions, symptoms plus medication dates/time stamps, reminders; or patient 1500 objective data via blood analyzer, spirometer, pulse oximeter, glucometer, temperature sensor, BP, EKG, ECG, EEG, ingestible capsule, ambulatory infusion pump, activity level monitor.

The invention may include a secure Server which provides immediate worldwide access (wired or wirelessly) to patient/client data, enables commands/alarms to be transmitted to the patient's/client's monitoring equipment, and makes an intelligent graphical user interface ("GUI") available for command/control/display/monitoring.

The intelligent GUI may have the capability to process the data of one or more patients/clients and provide tables/graphs/charts/alarms that help the prioritization of reviewing patient/client status, as well as provide a simple dashboard for each patient to help medical personnel quickly grasp the overall status of patients.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

DETAILED DESCRIPTION OF THE INVENTION

The following describes the details of the invention. Although the following description will proceed with reference being made to illustrative embodiments, many alternatives, modifications, and variations thereof will be apparent to those skilled in the art. Accordingly, it is intended that the claimed subject matter be viewed broadly. Examples are provided as reference and should not be construed as limiting. The term "such as" when used should be interpreted as "such as, but not limited to."

Figure 1:
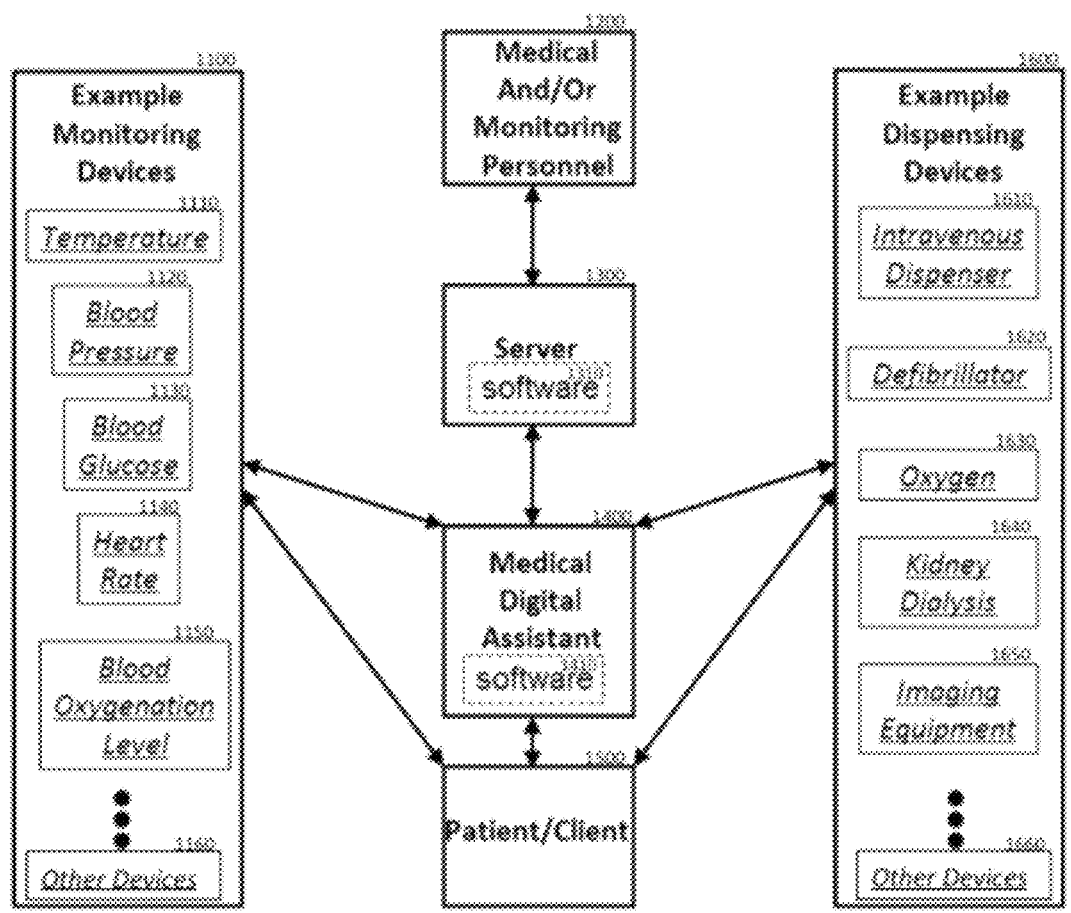
FIG. 1: This is a block diagram showing the embodiments of the invention including the components, interfaces, and software blocks in accordance with the teachings of the present invention.
Figure 2:
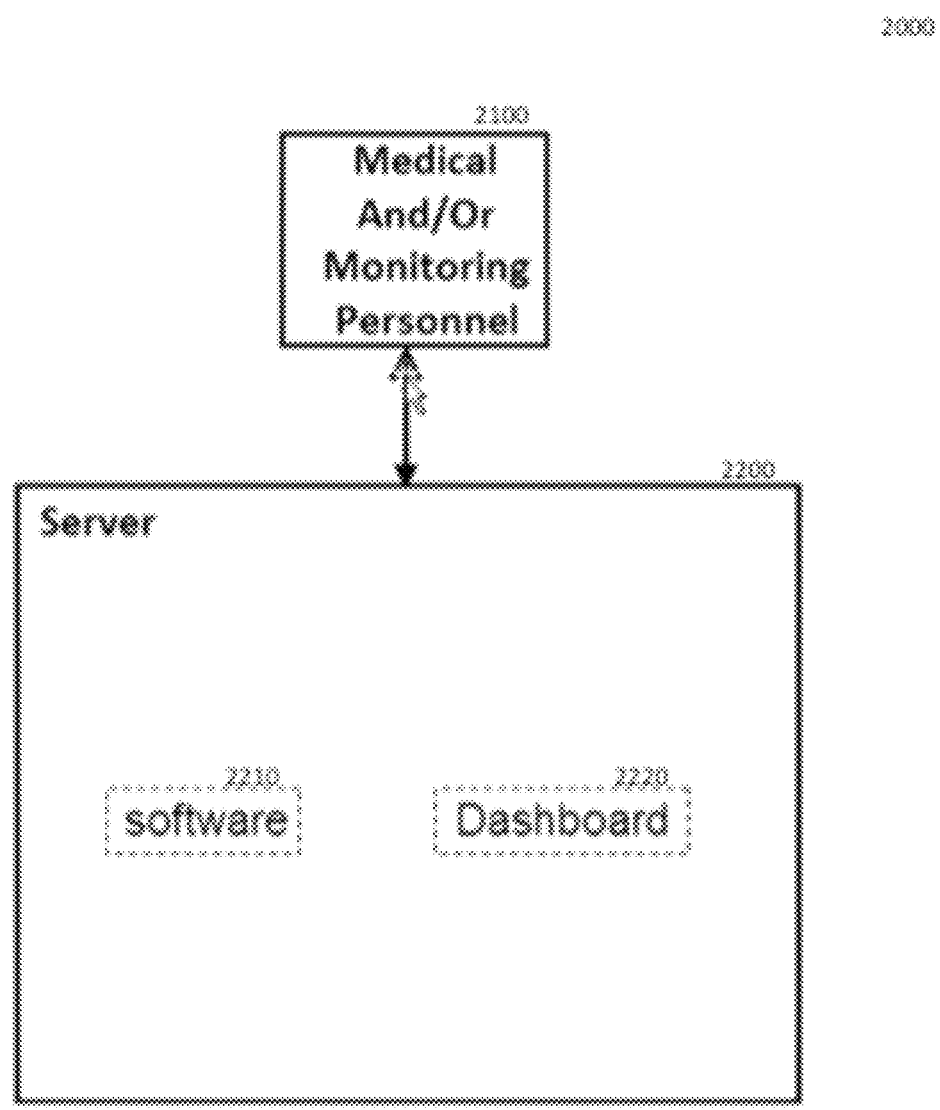
FIG. 2: This is a close up view of the block diagram illustrating the interface between the server and monitoring personnel, as well as the dashboard, in accordance with the teachings of the present invention.
Figure 3:
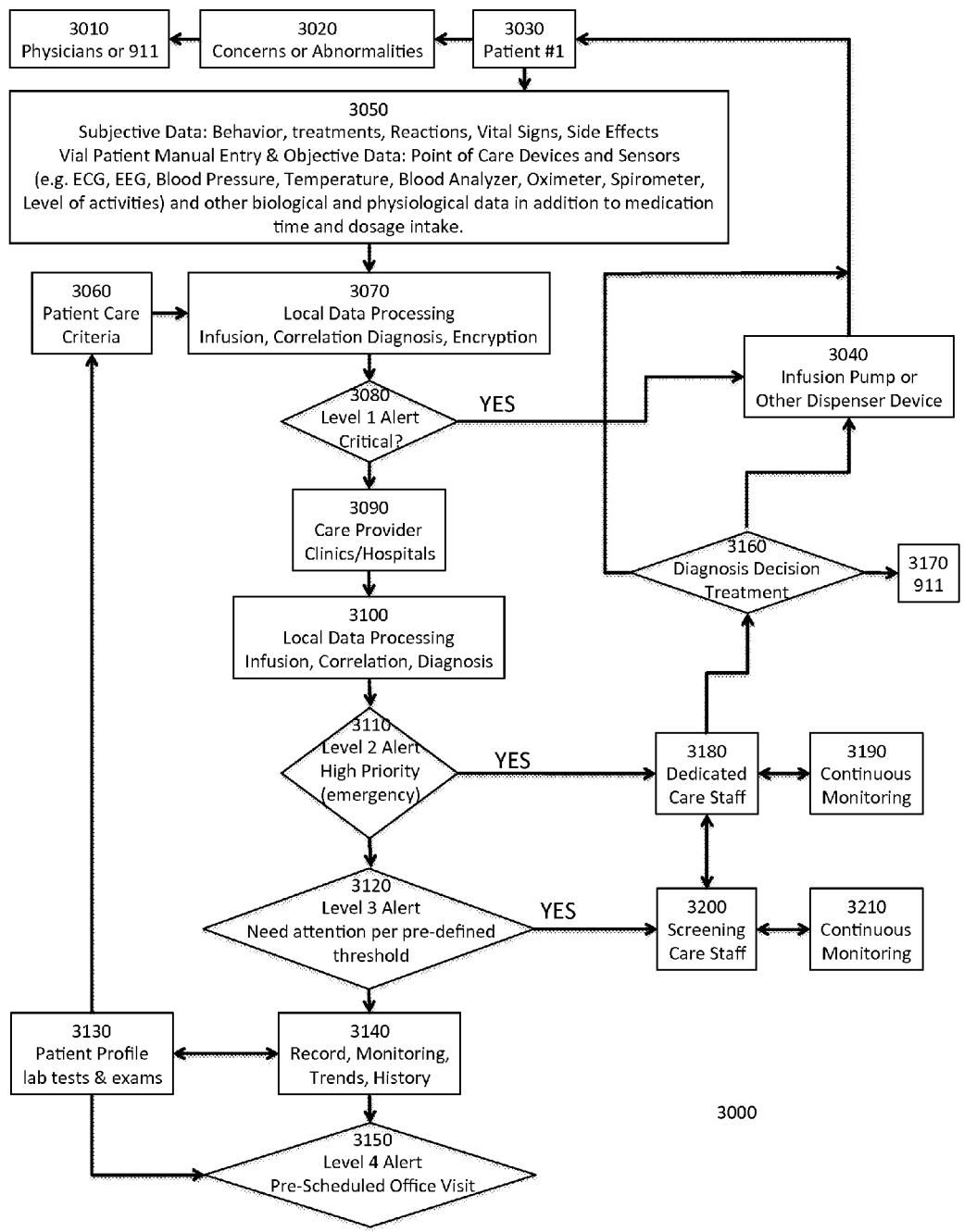
FIG. 3: This is a process flow diagram illustrating how the invention is used to obtain, transmit, collect, analyze, and report data to enhance medical diagnosis and treatment in accordance with the teachings of the present invention.
Figure 4:
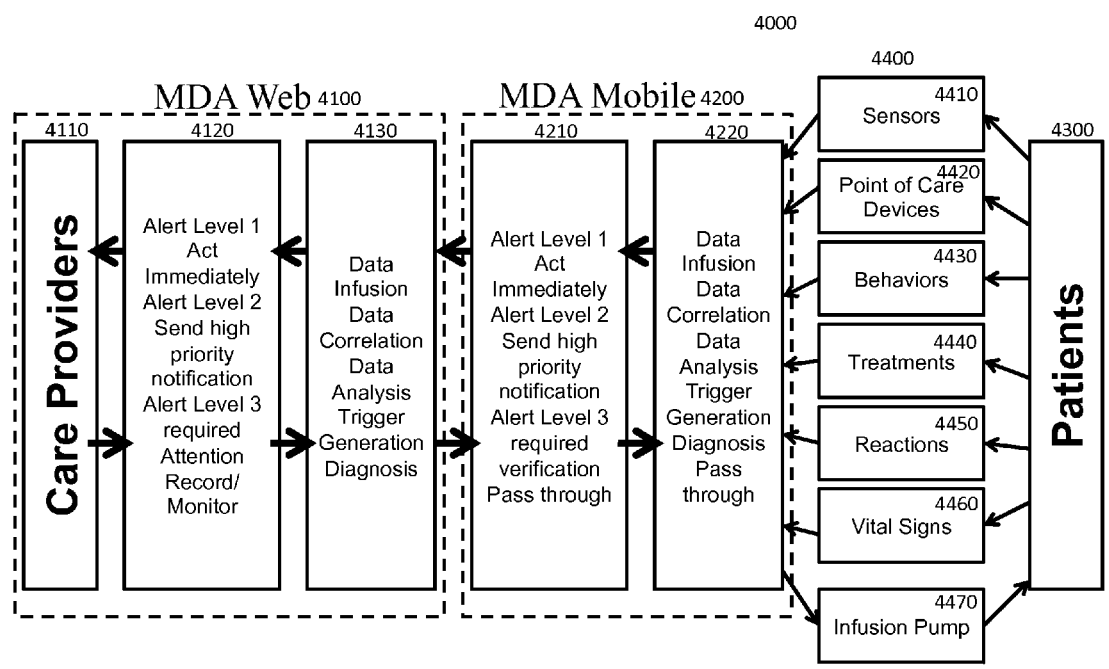
FIG. 4: This is an alternative view illustrating the components of the invention and how they are integrated and interact with subjects and monitoring personnel in accordance with the teachings of the present invention.

FIGS. 1 and 2 depict the components of the system. FIG. 3 and depict the data, process and control flow between the subsystems. The major subsystems of the invention include the Medical Digital Assistant ("MDA") 1400, Server 1300 and 2200, Monitoring Devices 1100, Dispensing Devices 1600, Dashboard 2220, and Application Software 1310 and 2210. For convenience, a medical example is illustrated and discussed. However, due to the multi-purpose use of this invention, "Individual" could be used to replace "Patient", and "Police" or "Monitoring" could be used to replace "Medical"; making this invention useful for a multitude of specific monitoring, management, care, maintenance, and control applications of individuals.

The invention enables a low cost solution based on an off-the-shelf hand held computer so there is no need to develop an expensive custom made hardware and multiple device functionalities are enabled into one MDA 1400 handheld device. Furthermore, the invention provides for subjective and objective patient 1500 data collection with the system interfaced with point-of-care wired and/or wireless devices for capturing objective data collection such as level of activities, spirometer, thermometer, blood pressure, and EKG, or with a simple graphic interface for patients to enter subjective data such as level of pain, describe the pain, number of days out of work, level of wellness, etc. in one handheld device. The system also enables real-time interactive connection via high bandwidth data, video stream, messages, voice with exchange enabled between patients and healthcare professionals real-time over 3G and 4G technologies wireless data networks. The system further enables secure patient 1500 data handling with data encryption on the handheld device. All data gets uploaded and purged out from the handheld device to another secure centralized location via wired or wireless connectivity. Device privacy is assured by use of unique user identification, audit control with reports of data usage, and the consistent enforcement of HIPAA security and encryption policies.

The system includes an easy-to-view, easy-to-use interface for simple and logical application—even for patients with no computer skills. Maintenance and support of the system is efficient with remote management and support via secure, professional system maintenance and IT support for both healthcare professionals and patients. The system is portable and pocket-able providing for an easy to carry monitoring system that automatically synchronizes to a centralized database. The two-way communication built into the system enables nurses, physicians, researchers, patients, other healthcare and plan providers enjoy secure communications via video, message, voice, email and fax.

The invention integrates with existing electronic medical records ("EMR") through standard and/or proprietary interfaces, keeping records in one place and reducing the amount of paper storage. Easy access to trending reports allows healthcare providers to better visualize patient 1500 activity and manage therapies. Two-way communication enables more efficient, timely communication between health providers and patients. Physiological data portrays a truly accurate statistical update, which is sometimes different from what a patient 1500 indicates.

The invention enables monitoring of key indicators anywhere, anytime, reducing the need for office visits and/or hospitalization. There are many benefits to this invention such as: More life balance, regardless of the diagnosis or health condition; When a patient 1500 knows they are monitored, including consistent two-way communication with their health provider, it helps ease the stress of an illness, provide peace of mind, and promote quicker healing; Patient 1500 data collected by electronic systems has consistently demonstrated a reduction in data variance when compared to data collected on paper. This means studies can contain smaller cohorts, saving significant time and cost; Automatic wireless synch-up removes the need for plug-in cables, or even to have a computer at home; User-friendly interface makes it simple for all ages and all levels of technical ability to monitor their condition and better manage their care; Better titration of therapy will yield better health outcomes; A resource center with illustrated reports helps patients 1500 better understand the trends and progress of their condition, to keep them informed and empowered; Automated non-compliance alerts support early intervention and save time through management by exception; Unnecessary visits are eliminated, yet enabling healthcare professionals to stay in contact with patients 1500; Less paperwork means reduced costs and more time for patient 1500 care; Better compliance means healthier patients 1500 with fewer office visits and hospital stays; A real-time connection with participants improves the ability to monitor and intervene quickly if adverse events occur; Connection directly to point-of-care devices—for example with ambulatory actigraphy devices, oxygen, heart or blood pressure monitors, etc.,—to collect and record data more objectively; Electronic data collection is more accurate, less costly, and reports can be collected and analyzed seamlessly. Time is not lost waiting for paper to arrive or for data to be entered. With real-time recording and collection—plus a time-stamp to increase accuracy—recall bias is reduced; The system not only collects and securely stores patients' data, but also supports dedicated application software to manage the study and conduct data analysis; The following describes the details of the invention.

FIG. 1 is a diagram of an exemplary embodiment for a system 1000 that gathers and analyzes data to monitor, track, and provide care. The major subsystems of the invention include the Medical Digital Assistant ("MDA") 1400, Server 1300 and 2200, Monitoring Devices 1100, Dispensing Devices 1600, Dashboard 2220, and Application Software 1310 and 2210. First, the Monitoring Devices 1100 are used to acquire any number of various multiple data parameters. Next, the Dispensing Devices 1600 have the capability of performing an act on the patient 1500, and/or also require monitoring of specific parameter(s). Next, the Medical Digital Assistant 1400 is the patient's 1500 main interface and is responsible for local control and coordination with the Monitoring 1100 or Dispensing 1600 Devices.

This invention, allows the use of any commercially available Monitoring Device which stores and transmits data based on any standard specification, such as PCI Express, USB, WiMax, LTE, WiFi, WWAN, WLAN, LAN, PAN and WPAN including but not limited 2.5G, 3G, 4G, WiFi, Bluetooth, USB, POTs, Ethernet and other proprietary WPAN RF interfaces. The Monitoring Devices 1100 acquires patient 1500 data. The Monitoring Devices 1100 may require action by the patient 1500, the MDA 1400, or may be autonomous. The Monitoring Devices 1100 may be directly attached to the patient 1500 and/or connect to the patient 1500 using wires, electrodes, wireless technologies, tubes, or some other technology. Any control or configuration of the Monitoring Devices 1100 is accomplished primarily by the MDA 1400 (wired or wirelessly) and may also include patient 1500 actions. The data from the Monitoring Devices 1100 is transmitted to the MDA 1400 (wired or wirelessly), where it is locally encrypted, processed, stored, and retransmitted to the Server 1300.

In some configurations of the invention, the use of Dispensing Devices 1600 to perform some action on the patient 1500, which may or may not also require monitoring one or more patient 1500 parameters. The Dispensing Devices 1600 may be directly attached to the patient 1500, may connect to the patient 1500 using wires, electrodes, wireless technologies, tubes, or some other technology. Any control or configuration of the Dispensing Devices 1600 is accomplished primarily by the MDA 1400 (wired or wirelessly) and may also include patient 1500 actions. Any relevant data from the Dispensing Devices 1600 is transmitted to the MDA 1400 (wired or wirelessly), where it is locally encrypted, processed, stored, and retransmitted to the Server 1300.

The MDA 1400 is a crucial central component of the entire system. The system supports one or more MDAs 1400, enabling simultaneous support of one or more patients/clients 1500. The MDA 1400 may be a commercially available portable computer such as a notebook PC, tablet, smart-phone, or personal digital assistant. In another embodiment the MDA 1400 may be a customized device. The MDA 1400 is supported by the Application Software 1310 and 2210, which includes the logic to coordinate data retrieval, storage, communication, processing, analysis, and reporting. The primary functions of the MDA 1400 include control and configuration of both Monitoring Devices 1100 as well as Dispensing Devices 1600. The MDA 1400 may also be used for processing, encrypting, and storing patient data as well as equipment status from the Monitoring Devices 1100 the Dispensing Devices 1600, as well as patient 1500 responses to MDA 1400 interrogations of the patient 1500. The MDA 1400 also is used in aggregating and compressing/decompressing data so as to minimize the data that must be transferred to/from the Server 1300, thus minimizing communications charges. The MDA 1400 also performs searching, connecting, and securely relaying data to/from the Server 1300 (wired or wirelessly). The MDA 1400 also is used in deleting confidential patient data from the MDA 1400, as well as other local equipment, after successfully relaying data to/from the Server 1300. The MDA 1400 is also used for processing and making local decisions, such as asking the patient 1500 questions regarding either patient 1500 or equipment status.

The MDA 1400 is also equipped with software 1310 that enables the use of a data fusion process to make decisions based on data collected from local equipment(s), as well as patient 1500 responses to MDA 1400 initiated interrogations. MDA 1400 decisions may include, but not limited to; asking the patient 1500 different questions based on previous responses or collected equipment data, changing the setup/configuration/choice of Monitoring Devices 1100 or Dispensing Devices 1600, sending alarms to Medical Personnel 1200 and 2100, making recommendations to Medical Personnel 1200 and 2100 to alter the patient 1500 treatment.

The MDA 1400 also provides information to the patient 1500 and medical Personnel 1200 and 2100 regarding malfunctioning equipment.

The MDA 1400 provides a single user-friendly mobile human interface to monitor and/or control various complex equipment(s), one that can accommodate the disabilities of the specific patient 1500 such as hearing, vision, cognitive, etc. Finally, the MDA 1400 provides patient 1500 prompts to take medication, eat, sleep, wake, bathe or dress a wound, show up for an appointment, call to make an appointment, seek emergency assistance, reduce physical activity, increase physical activity, call relatives and or friends to report status, etc.

Next the Server 1300 provides multiple features and functions such as providing a secure link for data transfer to and from one or more MDAs 1400. The Server 1300 also provides a long-term secure and redundant database for data collected from one or more MDAs 1400. The Server 1300 is available to act as the data processing engine to compress and decompress data to minimize the required storage for patient/client data records and minimize data transfer charges to/from the MDAs 1400, as well as to act on patient data and Medical Personnel 1200 and 2100 requests/commands. The Server 1300 is also a data repository that can be accessed worldwide, any time, from anywhere, to anyone having either internet, telephone, cell, or radio link. Finally, the Server 2200 also provides a Dashboard 2220, as illustrated in FIG. 2, and further described below.

Next, the Medical or Monitoring Personnel 1200 and 2100 include anyone that needs to interact with the patient 1500 or patient's data. This may include nurses, pharmacists, technicians, family members/friends, and even the patient 1500. Each of these entities would have secure access to only the data that is approved for the entity. For example, a doctor may have only access to patients 1500 assigned to himself, with everyone having differing levels of data access. A patient 1500 would have access to only his own limited data, while family/friends would have further reduced levels of data access—configurable by the patient 1500 or other authorized entity.

The Medical Personnel 1200 and 2100 may interact with the Server 2200 either directly (locally logged into the Server 2200) or remotely via a wired or wirelessly connected client. The client may include a personal computing device such as a PC, Laptop, Netbook, MDA 1400, Tablet computer or a telephone (cell or landline).

Next the Dashboard 2220 is an application that runs on the Server 2200, and interacts with the Medical Personnel 1200 and 2100 and the database that is locally maintained on the Server 2200. The Dashboard 2220 provides the client with a graphical GUI, possibly through a Client PC. FIG. 2 depicts the concept of the Dashboard 2220 that is presented to the Medical Personnel 1200 and 2100. This Dashboard 2220 provides a multitude of features and functions such as providing critical status summary screen(s) for multiple patients 1500, enabling Medical Personnel 1200 and 2100 to quickly and efficiently grasp the status of multiple patients 1500. The Dashboard 2220 may also provide detailed screen(s) for selected patients 1500; provide alarm(s) for patient 1500 status; and provide graphing functions of selected parameters for selected patients 1500, enabling graphical comparisons over selectable time periods.

The Dashboard 2220 allows for Medical Personnel 1200 and 2100 to change the treatment for a selected patient 1500, by resetting/reconfiguring the patient's local equipment, changing medications or dosage, issuing lab requests, requesting appointments or telephone calls, requesting intervention and/or review of patient 1500 data from other specialist. The Dashboard 2220 also allows for Medical Personnel 1200 and 2100 to set various thresholds for various parameters of selected patients 1500. For example, if the $O_2$ level of patient 1500 X falls below Y, then activate an alarm and dispense an ambulance.

The Dashboard 2220 also provides patient's medical history, which is securely accessible anytime/anywhere by authorized personnel. The Dashboard 2220 also provides a patient 1500 database that can be used to automatically fill out forms/questionnaires, request insurance/Medicare/Medicaid pre-approval or submit claims. The Dashboard 2220 may alert Medical Personnel 1200 and 2100 of improper/risky prescribed treatments for patients 1500 due to allergies, multiple prescription interactions, or from past/present data collected from the patient 1500; for example, prescription X has or has not worked in the past for patient Y.

Next the Application Software 1310 and 2210 ties all of the components together and provides the processes for the coordination of data storage, data compression, patient/client record aggregation and compression, transmission, analysis, and reporting. The Application Software 1310 and 2210 is applied to the MDA 1400 and the Server 1300, and possibly the Monitoring 1100 and Dispensing Devices 1600. On the MDA 1400, the Application Software 1310 and 2210 coordinates the data acquisition from the Monitoring 1100 and or Dispensing 1600 Devices. The process includes: Requesting data from the Monitoring 1100 and or Dispensing 1600 Devices, either on demand, at synchronized times, or upon manual request; Acquiring data from the Monitoring 1100 and/or Dispensing 1600 Devices; Encrypting and Decrypting data from the Monitoring 1100 and or Dispensing 1600 Devices; Data aggregation, compression/decompression between the MDA 1400 and Server 1300; Performing some data analysis, which may be supported locally by the MDA 1400 processor instead of transmitting and analyzing data on the Server 1300; Sending request to delete the data on the Monitoring 1100 and or Dispensing 1600 Devices; Sending the data acquired from the Monitoring 1100 and or Dispensing 1600 Devices to the Server 1300; Performing self-tests to make sure the MDA 1400 and Monitoring 1100 and or Dispensing 1600 Devices are working properly; Sending requests to the Server 1300 to indicate the results of self-tests, such as requests for further maintenance.

The Application Software 2210 on the Server 2200 coordinates the data acquisition from one or more MDAs 1400 and also executes data analysis and reporting through the Dashboard 2220. The process further include: Instructing the MDAs 1400 to request data from the Monitoring 1100 and or Dispensing 1600 Devices; Requesting data from the MDA 1400; Encrypting and Decrypting data from the MDA 1400; and performing data analysis. For example, the Server 1300 can determine whether a patient's vitals are within an acceptable range. The Server 1300 will transmit the data analysis in a report, such as the Dashboard 2220, to relevant people including the patient 1500, medical Personnel 1200 and 2100, etc.; Submitting data reports via the Dashboard 2220 via the world-wide-web, closed network, using a portable storage device, or printed to paper. In an alternative situation the Server 1300 may send emergency data reports to appropriate medical personnel 1200 and 2100. For example, the Server 1300 can be programmed to recognize emergency situations such as signs of an impending stroke and send a request for emergency medical personnel 1200 and 2100. Another example, is detecting when a person has fallen, for example by using accelerometer sensors which may transmit an immediate change in a persons height as an indication that the person has fallen, the Server 1300 may send a distress signal to local emergency personnel, or send a message to the person asking him to respond and indicate that the person has not lost consciousness. If there isn't an emergency situation, the Server 1300 will report the data to a Dashboard 2220, which can be accessed by the patient 1500, medical Personnel 1200 and 2100, or others.

Using advanced management technology the Application Software 1310 and 2210 can also be remotely managed and updated in a secure environment. This allows the Data Analytics System 1000 to be maintained and upgraded remotely and with reduced cost. For example, the Data Analytics System 1000 may be upgraded without the cost of changing the associated hardware such as the Monitoring 1100 and Dispensing 1600 Devices, MDA 1400, Server 1300, or Client PC.

The coordinated interaction of all these subsystems provides the useful, unique, and novel features/functions described above and comprise the invention described herein. A significant and diverse set of both Monitoring Devices 1100 and Dispensing 1600 Devices are currently commercially available for sale. The hardware functions provided by the MDA 1400 and the Server 1300 are also currently commercially available for sale. The coordination of all these subsystems is accomplished via the application running on the MDA 1400 interacting with the application running on the Server 1300. The client access to the Server 1300 can be provided by a custom client application, or can be provided by an existing commercially available client application such as an Internet browser.

The invention includes the method for conducting data acquisition, monitoring, analysis, and reporting to diagnose and treat medical conditions. For example, the invention may be used to diagnose and treat specific medical conditions such as fertility and congestive heart failure.

In one embodiment the invention is used to diagnose and treat infertility. Infertility, defined as the inability to become pregnant after one year of unprotected sex, affects about 6.1 million women in the US between the ages of 15 to 44 according to the CDC. For women trying to get pregnant, diagnosing ovulation is the first step to finding when they are most fertile. Currently, there are several indirect methods to predicting ovulation. These indirect methods involve measuring LH or estrogen levels in blood, urine, or saliva, charting basal body temperature ("BBT"), or analyzing cervical mucus. Of these methods, charting BBT is easy, cost effective and the least invasive.

Charting BBT, which can be self-administered at home, is a method to observe temperature patterns in the menstrual cycle. BBT exhibits a strong circadian rhythm, possibly due to an endogenous variation in the thermoregulatory set point. It can also vary depending on behavioral and external stimuli, including sleep, physical activity, ambient temperature, meals, and the menstrual cycle in women. When ovulation occurs, the corpus luteum releases progesterone, causing a 0.6 degree Fahrenheit increase in BBT. After several months of charting their BBT, women can approximate when they ovulate and thus are most fertile. Prior research has shown that the average true positive rate of charting BBT to diagnose ovulation is 90%.

Currently, women only measure their temperature immediately on waking, before rising, moving or taking food or drink. However, the change in BBT due to progesterone is best noticed at the lowest circadian thermogenic point, which occurs at approximately the 5th hour after sleep onset. It has been shown that in normal nocturnal sleep, BBT rises at the 6th hour after sleep onset.

This invention may be used to enhance the fertility treatment by first using the invention with a temperature sensor to monitor BBT continuously throughout the day. Next the invention is used with a sleep monitoring device continuously throughout the day. The invention is used to survey the women's lifestyle habits, including hour/quality of sleep, diet, exercise, alcohol/substance use, and emotional/stress levels. Next medical Personnel 1200 and 2100 can use the data captured continuously and the correlation of these data to detect an accurate ovulation window.

In another embodiment, the invention may be used to treat congestive heart failure. Approximately 5.8 million people in the United States have heart failure. The most common causes of heart failure are coronary artery disease, high blood pressure, and diabetes. Typical co-morbidities that contribute to HF patient 1500's de-compensation include: High cholesterol, High blood pressure, Diabetes, Cigarette smoking, Overweight and obesity, Poor diet, Physical inactivity, and Alcohol use.

The invention may be used to capture multiple data streams in order to detect early heart failure symptoms to prevent serious implications. For example, the invention may be used to capture and monitor all of the following data streams simultaneously and continuously: monitor BP three times a day via BP Monitor device; monitor activity level during the day via Pedometer; monitor oxygen level for about 3 minutes a day while patient 1500 walking via Oximeter; monitor weight once every morning via a weight scale; monitor EKG 24 hrs a day via a wireless sensor; and monitor time of medication and effectiveness, and any medication side effects. The invention is then used to conduct automated data analysis and correlation to detect any possible abnormalities.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Other modifications, variations, and alternatives are also possible. Accordingly, the claims are intended to cover all such equivalents.

The invention claimed is:

1. A method comprising: using a monitoring device to acquire data from a patient; using a dispensing device to perform actions on a patient; transmitting data from the monitoring device or dispensing device to a medical digital assistant; using the medical digital assistant to coordinate data retrieval, storage, communication, processing, analysis, and reporting; performing actions on the patient based on the data analysis results using the monitoring device or dispensing devices controlled or configured by the medical digital assistant; and wherein the data monitored includes monitoring blood pressure with a blood pressure monitoring device at least three times per day, monitoring activity level continuously throughout the day with a pedometer, monitoring oxygen levels for at least three minutes a day with an oximeter, monitoring weight once every day with a scale, monitoring EKG continuously every day with a remote EKG sensor, and monitoring the time, effectiveness, and side effects of medication.

2. A method according to claim 1, wherein the patient is a human child or adult.

3. A method according to claim 1, wherein the patient is a non-human animal.

4. A method according to claim 1, wherein the actions by the medical digital assistant include asking the patient different questions based on previous responses.

5. A method according to claim 1, wherein the actions by the medical digital assistant include changing the setup, configuration, or selected monitoring or dispensing devices.

6. A method according to claim 1, wherein the actions include sending alarms to medical personnel.

7. A method according to claim 1, wherein the actions include requests to alter the patient's treatment comprising at least one of resetting or reconfiguring the patient's dispensing devices, changing medications or dosage levels, issuing lab request, requesting appointments or telephone calls, requesting intervention and review from other personnel, or setting thresholds for various data parameters.

8. A method according to claim 1, wherein the data monitored includes the basal body temperature and sleep duration of a female patient to detect an accurate ovulation duration.

9. A method according to claim 1, wherein the data monitored is critical for detecting chronic disease symptoms comprising least one of cholesterol levels, blood pressure, calories, physical activity, and alcohol levels.

10. A method according to claim 9, wherein the chronic diseases include heart failure, diabetes, hypertension, and chronic obstructive pulmonary disorders.

11. The method according to claim 1, wherein the method is remotely managed and updated remotely.

12. The method according to claim 1, wherein the analysis is performed locally by the medical digital assistant instead of transmitting and analyzing data on the server.

13. The method according to claim 1, wherein the requests to the monitoring and dispensing devices to perform actions on the patient are input by the patient, medical personnel, or other authorized users.

14. The method according to claim 1, wherein the requests to the monitoring and dispensing devices to perform actions on the patient are based on pre-programmed situations.

15. The method according to claim 14, wherein the pre-programmed situation is detecting signs of an impending acute medical emergency.

16. The method according to claim 14, wherein the automatic action is a request for emergency medical personnel.

* * * * *